United States Patent
Fandrick et al.

(10) Patent No.: US 9,029,592 B2
(45) Date of Patent: May 12, 2015

(54) PROCESS FOR PREPARING CARBOXAMIDINE COMPOUNDS

(71) Applicants: Keith R. Fandrick, Sandy Hook, CT (US); Joe Ju Gao, Southbury, CT (US); Jason Alan Mulder, New Milford, CT (US); Nitinchandra D. Patel, Danbury, CT (US); Xingzhong Zeng, New Milford, CT (US)

(72) Inventors: Keith R. Fandrick, Sandy Hook, CT (US); Joe Ju Gao, Southbury, CT (US); Jason Alan Mulder, New Milford, CT (US); Nitinchandra D. Patel, Danbury, CT (US); Xingzhong Zeng, New Milford, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 13/761,434

(22) Filed: Feb. 7, 2013

(65) Prior Publication Data

US 2013/0211130 A1 Aug. 15, 2013

Related U.S. Application Data

(60) Provisional application No. 61/596,767, filed on Feb. 9, 2012.

(51) Int. Cl.

| | |
|---|---|
| *C07C 269/00* | (2006.01) |
| *C07C 259/14* | (2006.01) |
| *C07C 251/40* | (2006.01) |
| *C07C 47/24* | (2006.01) |
| *C07C 271/12* | (2006.01) |
| *C07C 29/143* | (2006.01) |
| *C07C 45/27* | (2006.01) |
| *C07C 249/08* | (2006.01) |
| *C07F 5/02* | (2006.01) |

(52) U.S. Cl.
CPC ............... *C07C 259/14* (2013.01); *C07C 47/24* (2013.01); *C07C 251/40* (2013.01); *C07C 271/12* (2013.01); *C07C 29/143* (2013.01); *C07C 269/00* (2013.01); *C07C 45/27* (2013.01); *C07C 249/08* (2013.01); *C07B 2200/07* (2013.01); *C07C 2101/02* (2013.01); *C07F 5/025* (2013.01)

(58) Field of Classification Search
None
See application file for complete search history.

(56) References Cited

U.S. PATENT DOCUMENTS 5,072,037 A 12/1991 Weber et al.

FOREIGN PATENT DOCUMENTS

| WO | WO8601800 | * | 3/1986 | ............... C07F 7/22 |
| WO | 2008050200 A1 | | 5/2008 | |
| WO | 2008117148 A1 | | 10/2008 | |
| WO | WO2009029499 A1 | * | 3/2009 | ........... A61K 31/506 |

OTHER PUBLICATIONS

Bagutski, V. Angewandte Chemie International Edition, 2010, 49, 5142-5145.*
Bagutski, V. Angewandte Chemie International Edition, 2010, 49, 5142-5145—Supporting Information.*
Chen, A. Journal of Organic Chemistry, 1999, 64, 9704-9710.*
Brown, Herbert C. et al. "Organoboranes. 41. Reaction of Organoboranes with (Dichloromethy)lithium. Scope and Limiations. Synthesis of Homologated Primary and Secondary Alcohols." The Journal of Organic Chemistry (1985) vol. 50, No. 21, pp. 4032-4036.
Czekelius, Constantin et al. "Convenient Transformation of Optically Active Nitroalkanes into Chiral Aldoximes and Nitriles" Angewandte Chemie International Edition (2005) vol. 44, pp. 612-615.
Eastwood, Paul et al. "Indolin-2-one p38a inhibitors III: Bioisosteric amide replacement" Bioorganic & Medicinal Chemistry Letters (2011) vol. 21, pp. 6253-6257.
International Search Report for PCT/US2013/025053 mailed Apr. 22, 2013.
Nave, Stefan et al. "Protodeboronation of Tertiary Boronic Esters: Asymmetric Synthesis of Tertiary Alkyl Stereogenic Centers" Journal of the American Chemical Society (2010) vol. 132, No. 48, pp. 17096-17098.
Wang, Zhihui et al. "CF3CO2ZnEt-mediated highly regioselective rearrangement of bronnohydrins to aldehydes" Tetrahedron Letters (2011) vol. 52, No. 45 pp. 5968-5971.

* cited by examiner

*Primary Examiner* — Karl J Puttlitz
*Assistant Examiner* — Amy C Bonaparte
(74) *Attorney, Agent, or Firm* — Michael P. Morris; Usha R. Patel

(57) ABSTRACT

The present invention relates to a process of making a compound of formula (I):

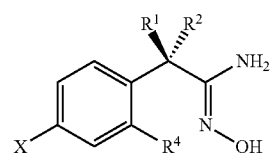

Wherein, $R^1$, $R^2$, $R^4$ and X are as defined herein.

23 Claims, No Drawings

PROCESS FOR PREPARING CARBOXAMIDINE COMPOUNDS

This application relates to a process of preparing chiral carboxamidine compounds. These carboxamidines can be used to prepare pharmaceutically active compounds, such as FLAP inhibitors, containing an oxadiazole ring.

BACKGROUND OF THE INVENTION

Carboxamidine intermediates can be used to prepare oxadiazole compounds which are inhibitors of five lipoxygenase activating protein (FLAP) and are thus useful for treating a variety of diseases and disorders that are mediated or sustained through the activity of leukotrienes including asthma, allergy, rheumatoid arthritis, multiple sclerosis, inflammatory pain, acute chest syndrome and cardiovascular diseases including atherosclerosis, myocardial infarction and stroke. The preparation of oxadiazole compounds via a carboxamidine intermediate is disclosed in U.S. application Ser. No. 13/208,582 "Oxadiazole Inhibitors of Leukotriene Production", filed Aug. 12, 2011.

DESCRIPTION OF THE INVENTION

The present invention is directed to a process of making a compound of formula I:

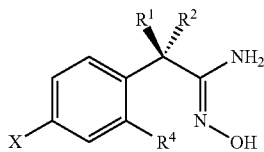

I the process comprising:

a) reducing a carbonyl compound of formula II under asymmetric reduction conditions, such as asymmetric hydrogenation or asymmetric transfer hydrogenation using, but not limited to, formic acid/triethylamine or potassium hydroxide/isopropyl alcohol, in the presence of a suitable catalyst, in a suitable solvent, to provide a compound of formula III:

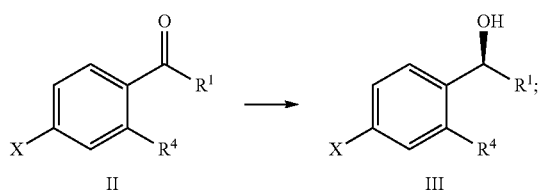

b) reacting the compound of formula III with a $C_{1-5}$ dialkyl-carbamoyl chloride, in a suitable solvent, in the presence of a suitable base, to provide a carbamate of formula IV, wherein R is $C_{1-5}$ alkyl:

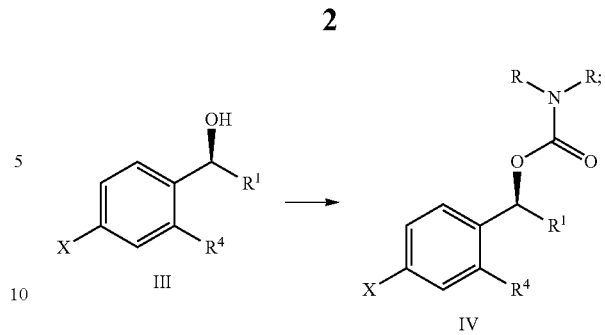

c) reacting the compound of formula IV with a suitable borane, boronic acid or boronic acid ester, such as $R^2$—B(YRa)(YRb), in a suitable solvent, in the presence of a suitable base, at a suitable temperature, to provide an intermediate of formula V, wherein Y is a bond or oxygen, Ra and Rb are each independently hydrogen, $C_{1-5}$ alkyl, $C_{3-8}$ cycloalkyl, or Ra and Rb together with the atoms to which they are attached form a ring which is optionally substituted with 1-6 substituents selected from $C_{1-3}$ alkyl, $C_{3-6}$ cycloalkyl, and $C_{1-3}$ alkoxyl:

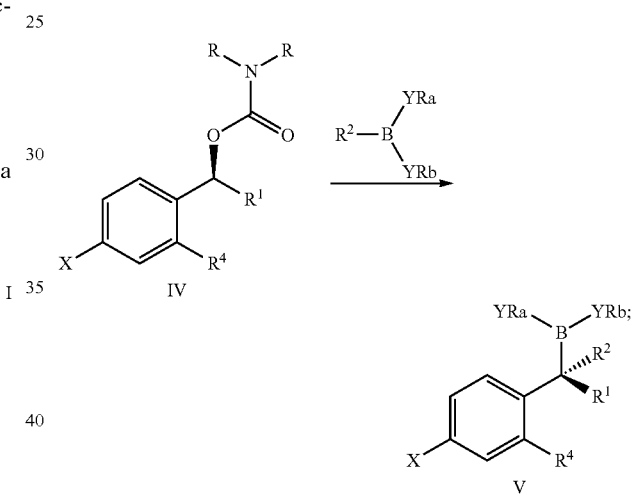

d) reacting the compound of formula V with a methylene equivalent such as, but not limited to, dichloromethane, in the presence of a suitable base such as metal-$C_{1-5}$ dialkylamides or metal-$C_{1-5}$ dialkyl bases wherein the metal is lithium, sodium, potassium, calcium or magnesium, in a suitable solvent, in the presence of an oxidizing agent such as, but not limited to, hydrogen peroxide, to provide a carboxaldehyde of formula VI:

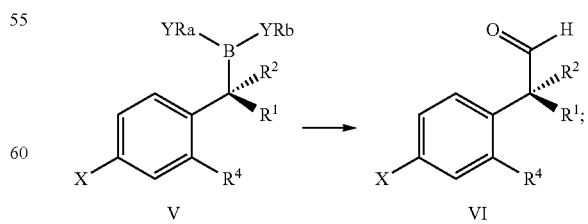

e) reacting the carboxaldehyde of formula VI with hydroxylamine, in a suitable solvent, to provide an oxime of formula VII:

and f) reacting the oxime of formula VII with an acid, such as hydrogen chloride, followed by the reaction with reagents such as N-chlorosuccinimide and ammonium hydroxide, in a suitable solvent, to provide a carboxamidine of formula I:

wherein:
$R^1$ and $R^2$ are each independently hydrogen, $C_{1-7}$ alkyl or $C_{3-10}$ carbocycle, with the proviso that both $R^1$ and $R^2$ are not simultaneously hydrogen;
$R^4$ is hydrogen, $C_{1-3}$ alkyl, halogen or nitrile; and
X is halogen.

In another embodiment, the invention relates to a process of making a compound of formula I, according to the previous embodiment, wherein:
$R^1$ and $R^2$ are each independently methyl, ethyl, isopropyl, cyclopropyl, cyclobutyl or cyclopentyl;
$R^4$ is hydrogen, methyl or nitrile; and
X is chloro, bromo or iodo.

Non-limiting examples of asymmetric reduction conditions in step (a) include, asymmetric hydrogenation, transfer hydrogenation using formic acid/base such as triethylamine and potassium hydroxide/isopropyl alcohol. Non-limiting examples of solvents useful in step (a) include acetonitrile, tetrahydrofuran, 1,4 dioxane or a mixture thereof.

Non-limiting examples of solvents useful in step (b) include acetonitrile, dichloromethane, tetrahydrofuran, dimethylformamide, N-methylpyrrolidinone, ethyl acetate, isopropylacetate, dimethylsulfoxide (DMSO), 1,4 dioxane or a mixture thereof. Non-limiting examples of bases useful in step (b) include 1,8-diazabicycloundec-7-ene (DBU), triethylamine, pyridine, 4-methylmorpholine, diisopropylethylamine and dimethylamine.

Non-limiting examples of bases useful in step (c) include butyllithium, sec. butyllithium, tert.butyllithium, lithiumdiisopropylamide (LDA), lithium hexamethyldisilazide (LiHMDS) and lithium tetramethylpiperidine (LiTMP). Non-limiting examples of solvents useful in step (c) include diethyl ether, toluene, MTBE, cyclopentyl methyl ether, tetrahydrofuran, DME, diisopropyl ether, 1,4 dioxane, Me-THF or a mixture thereof.

Non-limiting examples of bases useful in step (d) include butyllithium, sec. butyllithium, tert.butyllithium, lithiumdiisopropylamide (LDA), lithium hexamethyldisilazide (LiHMDS) and lithium tetramethylpiperidine (LiTMP). Non-limiting examples of oxidizing agents useful for step (d) include hydrogen peroxide, t-butyl-OOH and m-chloroperbenzoic acid. Non-limiting examples of solvents useful in step (d) include diethyl ether, toluene, MTBE, cyclopentyl methyl ether, tetrahydrofuran, 1,4 dioxane, toluene, heptane or a mixture thereof.

Non-limiting examples of solvents useful in step (e) include methanol, ethanol, isopropyl alcohol, sec. butanol or a mixture thereof.

Non-limiting examples of solvents useful in step (f) include acetonitrile, dichloromethane, tetrahydrofuran, diethyl ether, 1,4 dioxane or a mixture thereof.

The process of the invention provides a stereoselective route, with high stereoselectivity, for preparing the compounds of formula I, which are key intermediates in the synthesis of FLAP inhibitors containing the oxadiazole ring disclosed in U.S. application Ser. No. 13/208,582 "Oxadiazole Inhibitors of Leukotriene Production", filed Aug. 12, 2011.

A carboxamidine of formula I may be converted to an oxadiazole of formula VIII as outlined in Scheme A below.

Scheme A

As illustrated in scheme A, reaction of the carboxamidine of formula I with an acid chloride $R^5COCl$, in a suitable solvent, in the presence of a suitable base, provides an oxadiazole compound of formula VIII:
wherein $R^5$ is $C_{1-6}$ alkyl, $C_{3-10}$ carbocycle, 5-11 membered heterocycle, aryl, 5-11 membered heteroaryl, —C(O)—$R^6$, hydroxy or —$NR^7R^8$, wherein each $R^5$ is optionally independently substituted with one to three groups selected from $R^9$, $R^{10}$ and $R^{11}$;
$R^6$ is $C_{3-8}$ heterocycle or —NH-5-6 membered heterocycle, each optionally independently substituted with one to three groups selected from $R^9$, $R^{10}$ and $R^{11}$;
$R^7$ and $R^8$ are each independently hydrogen or $C_{1-6}$ alkyl;
$R^9$, $R^{10}$ and $R^{11}$ are independently selected from
(a) —H,
(b) —OH,
(c) halogen,
(d) —CN,
(e) —CF$_3$,
(f) $C_{1-6}$alkyl optionally substituted with one to three —OH, —N($R^{12}$)($R^{13}$), 3-6 membered heterocycle, $C_{1-6}$alkoxy, —C(O)N($R^{12}$)($R^{13}$) or —S(O)$_n$C$_{1-6}$alkyl,
(g) $C_{1-6}$alkoxy,
(h) —N($R^{12}$)($R^{13}$),
(i) —S(O)$_n$C$_{1-6}$ alkyl,
(j) —CO$_2R^{12}$,
(k) —C(O)N($R^{12}$)($R^{13}$), (l) —S(O)$_2$N(R$^{12}$)(R$^{13}$),
(m) a 3-10 membered heterocyclic group optionally substituted with one to three C$_{1-6}$ alkyl groups,
(n') oxo,
(o) —C(O)—C$_{1-3}$ alkyl;

R$^{12}$ and R$^{13}$ are each independently selected from —H, —C$_{1-6}$alkyl, C(O)C$_{1-6}$alkyl, and a 3-6 membered heterocyclic group, each of which is optionally independently substituted with one to three C$_{1-6}$alkyl groups, —OH, C$_{1-6}$alkoxy, —C(O)N(R$^{14}$)(R$^{15}$), —S(O)$_n$C$_{1-6}$alkyl, CN, a 3-6 membered heterocyclic group, —OC$_{1-6}$alkyl, CF$_3$, or;

R$^{12}$ and R$^{13}$ taken together with the nitrogen ring to which they are attached form a heterocyclic ring optionally substituted with one to three —OH, CN, —OC$_{1-6}$alkyl or oxo;

R$^{14}$ and R$^{15}$ are each independently selected from —H and —C$_{1-6}$alkyl;

n is 0, 1 or 2;

Alternatively, reaction of a compound of formula I with an acid R$^5$COOH, in a suitable solvent, in the presence of carbonyl diimidazole, or other suitable amide coupling reagent, provides an oxadiazole compound of formula VIII which can then be converted to oxadiazole FLAP inhibitors disclosed in U.S. application Ser. No. 13/208,582 "Oxadiazole Inhibitors of Leukotriene Production", filed Aug. 12, 2011.

The invention relates to the use of any compounds described above containing one or more asymmetric carbon atoms including racemates and racemic mixtures, single enantiomers, diastereomeric mixtures and individual diastereomers. Isomers shall be defined as being enantiomers and diastereomers. All such isomeric forms of these compounds are expressly included in the present invention. Each stereogenic carbon may be in the R or S configuration, or a combination of configurations.

Some of the compounds of the invention can exist in more than one tautomeric form. The invention includes methods using all such tautomers.

All terms as used herein in this specification, unless otherwise stated, shall be understood in their ordinary meaning as known in the art. For example, "C$_{1-6}$ alkoxy" is a C$_{1-6}$ alkyl with a terminal oxygen, such as methoxy, ethoxy, propoxy, butoxy. All alkyl, alkenyl, and alkynyl groups shall be understood as being branched or unbranched where structurally possible and unless otherwise specified. Other more specific definitions are as follows:

The term "alkyl" refers to both branched and unbranched alkyl groups. It should be understood that any combination term using an "alk" or "alkyl" prefix refers to analogs according to the above definition of "alkyl". For example, terms such as "alkoxy", "alkylhio" refer to alkyl groups linked to a second group via an oxygen or sulfur atom. "Alkanoyl" refers to an alkyl group linked to a carbonyl group (C=O).

In all alkyl groups or carbon chains, one or more carbon atoms can be optionally replaced by heteroatoms such as O, S or N. It shall be understood that if N is not substituted then it is NH. It shall also be understood that the heteroatoms may replace either terminal carbon atoms or internal carbon atoms within a branched or unbranched carbon chain. Such groups can be substituted as herein above described by groups such as oxo to result in definitions such as but not limited to: alkoxycarbonyl, acyl, amido and thioxo. As used herein, "nitrogen" and "sulfur" include any oxidized form of nitrogen and sulfur and the quaternized form of any basic nitrogen. For example, for a —S—C$_{1-6}$ alkyl radical, unless otherwise specified, shall be understood to include —S(O)—C$_{1-6}$ alkyl and —S(O)$_2$—C$_{1-6}$ alkyl.

The term "C$_{3-10}$ carbocycle" refers to a nonaromatic 3 to 10-membered (but preferably, 3 to 6-membered) monocyclic carbocyclic radical or a nonaromatic 6 to 10-membered fused bicyclic, bridged bicyclic, or spirocyclic carbocyclic radical. The C$_{3-10}$ carbocycle may be either saturated or partially unsaturated, and the carbocycle may be attached by any atom of the cycle which results in the creation of a stable structure. Non-limiting examples of 3 to 10-membered monocyclic carbocycles include cyclopropyl, cyclobutyl, cyclopentyl, cyclopentenyl, cyclohexyl, cyclohexenyl, cycloheptanyl, cycloheptenyl, and cyclohexanone. Non-limiting examples of 6 to 10-membered fused bicyclic carbocyclic radicals include bicyclo[3.3.0]octane, bicyclo[4.3.0]nonane, and bicyclo[4.4.0]decanyl (decahydronaphthalenyl). Non-limiting examples of 6 to 10-membered bridged bicyclic carbocyclic radicals include bicyclo[2.2.2]heptanyl, bicyclo[2.2.2]octanyl, and bicyclo[3.2.1]octanyl. Non-limiting examples of 6 to 10-membered spirocyclic carbocyclic radicals include but are not limited to spiro[3,3]heptanyl, spiro[3,4]octanyl and spiro[4,4]heptanyl.

The term "C$_{6-10}$ aryl" or "aryl" refers to aromatic hydrocarbon rings containing from six to ten carbon ring atoms. The term C$_{6-10}$ aryl includes monocyclic rings and bicyclic rings where at least one of the rings is aromatic. Non-limiting examples of C$_{6-10}$ aryls include phenyl, indanyl, indenyl, benzocyclobutanyl, dihydronaphthyl, tetrahydronaphthyl, naphthyl, benzocycloheptanyl and benzocycloheptenyl.

The term "5 to 11-membered heterocycle" refers to a stable nonaromatic 4-8 membered monocyclic heterocyclic radical or a stable nonaromatic 6 to 11-membered fused bicyclic, bridged bicyclic or spirocyclic heterocyclic radical. The 5 to 11-membered heterocycle consists of carbon atoms and one or more, preferably from one to four heteroatoms chosen from nitrogen, oxygen and sulfur. The heterocycle may be either saturated or partially unsaturated. Non-limiting examples of nonaromatic 4-8 membered monocyclic heterocyclic radicals include tetrahydrofuranyl, tetrahydropyranyl, oxetanyl, azetidinyl, pyrrolidinyl, pyranyl, tetrahydropyranyl, dioxanyl, thiomorpholinyl, 1,1-dioxo-1λ$^6$-thiomorpholinyl, morpholinyl, piperidinyl, piperazinyl, and azepinyl. Non-limiting examples of nonaromatic 6 to 11-membered fused bicyclic radicals include octahydroindolyl, octahydrobenzofuranyl, and octahydrobenzothiophenyl. Non-limiting examples of nonaromatic 6 to 11-membered bridged bicyclic radicals include 2-azabicyclo[2.2.1]heptanyl, 3-azabicyclo[3.1.0]hexanyl, and 3-azabicyclo[3.2.1]octanyl. Non-limiting examples of nonaromatic 6 to 11-membered spirocyclic heterocyclic radicals include 7-aza-spiro[3,3]heptanyl, 7-spiro[3,4]octanyl, and 7-aza-spiro[3,4]octanyl.

The term "5 to 11-membered heteroaryl" shall be understood to mean an aromatic 5 to 6-membered monocyclic heteroaryl or an aromatic 7 to 11-membered heteroaryl bicyclic ring where at least one of the rings is aromatic, wherein the heteroaryl ring contains 1-4 heteroatoms such as N, O and S, Non-limiting examples of 5 to 6-membered monocyclic heteroaryl rings include furanyl, oxazolyl, isoxazolyl, oxadiazolyl, thiazolyl, pyrazolyl, pyrrolyl, imidazolyl, tetrazolyl, triazolyl, thienyl, thiadiazolyl, pyridinyl, pyrimidinyl, pyridazinyl, pyrazinyl, triazinyl, and purinyl. Non-limiting examples of 7 to 11-membered heteroaryl bicyclic heteroaryl rings include benzimidazolyl, quinolinyl, dihydro-2H-quinolinyl, isoquinolinyl, quinazolinyl, indazolyl, thieno[2,3-d]pyrimidinyl, indolyl, isoindolyl, benzofuranyl, benzopyranyl, benzodioxolyl, benzoxazolyl and benzothiazolyl.

It will be understood that one to three carbon ring moieties in the each of the $C_{3-10}$ carbocyclic rings, the 5 to 11-membered heterocyclic rings, the nonaromatic portion of the bicyclic aryl rings, and the nonaromatic portion of the bicyclic heteroaryl rings can independently be replaced with a carbonyl, thiocarbonyl, or iminyl moiety, i.e., —C(=O)—, —C(=S)— and —C(=NR$^8$)—, respectively, where R$^8$ is as defined above.

The term "heteroatom" as used herein shall be understood to mean atoms other than carbon such as O, N, and S.

The term "halogen" as used in the present specification shall be understood to mean bromine, chlorine, fluorine or iodine. The definitions "halogenated", "partially or fully halogenated"; partially or fully fluorinated; "substituted by one or more halogen atoms", includes for example, mono, di or tri halo derivatives on one or more carbon atoms. For alkyl, a non-limiting example would be —CH$_2$CHF$_2$, —CF$_3$ etc.

Each alkyl, carbocycle, or the analogs thereof, described herein shall be understood to be optionally partially or fully halogenated.

The compounds of the invention are only those which are contemplated to be 'chemically stable' as will be appreciated by those skilled in the art. For example, a compound which would have a 'dangling valency', or a 'carbanion' are not compounds contemplated by the inventive methods disclosed herein.

General Synthetic Methods

The invention provides processes for making compounds of Formula (I) wherein unless specified otherwise, R$^1$, R$^2$, R$^4$, R and X in the Formulas below shall have the meaning of R$^1$, R$^2$, R$^4$, R and X in Formula (I) of the invention described herein above.

Optimum reaction conditions and reaction times may vary depending on the particular reactants used. Unless otherwise specified, solvents, temperatures, pressures, and other reaction conditions may be readily selected by one of ordinary skill in the art. Specific procedures are provided in the Synthetic Examples section. Typically, reaction progress may be monitored by thin layer chromatography (TLC), LC-MS or HPLC, if desired, and intermediates and products may be purified by chromatography on silica gel, recrystallization and/or preparative HPLC.

The example which follows is illustrative and, as recognized by one skilled in the art, particular reagents or conditions could be modified as needed for individual compounds without undue experimentation. Starting materials and intermediates used, in the Scheme below, are either commercially available or easily prepared from commercially available materials by those skilled in the art.

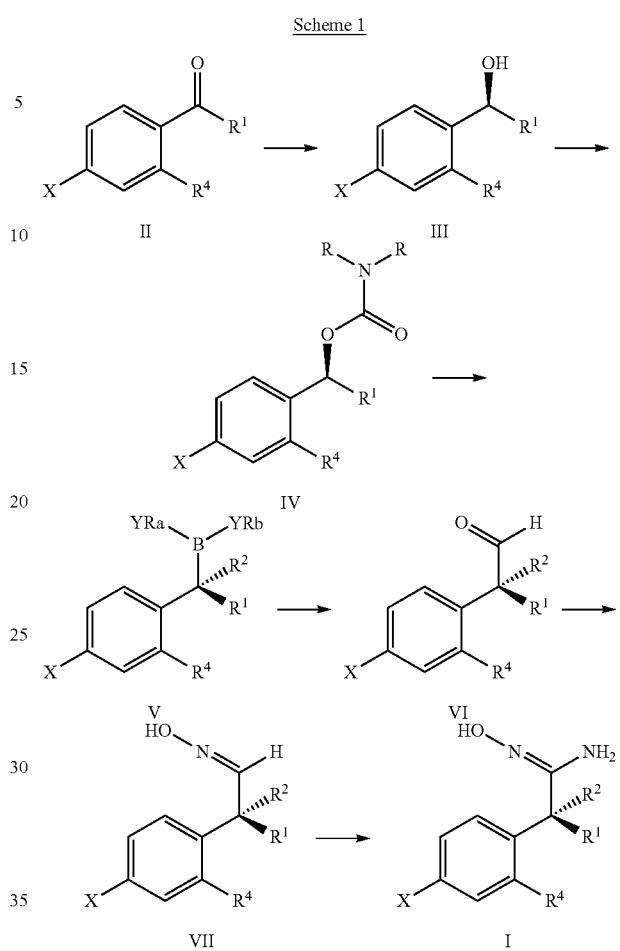

Scheme 1

As illustrated in scheme 1, reduction of a carbonyl compound of formula II under asymmetric reduction conditions, such as asymmetric hydrogenation or asymmetric transfer hydrogenation using, but not limited to, formic acid/triethylamine or potassium hydroxide/isopropyl alcohol, in the presence of a suitable catalyst, in a suitable solvent, provides a compound of formula III. Reaction of the compound of formula III with a $C_{1-5}$ dialkylcarbamoyl chloride, in a suitable solvent, in the presence of a suitable base, provides a carbamate of formula IV, wherein R is $C_{1-5}$ alkyl. Reaction of the compound of formula IV with a suitable borane, boronic acid or boronic acid ester, such as R$^2$—B(YRa)(YRb), in a suitable solvent, in the presence of a suitable base, provides an intermediate of formula V, wherein Y is a bond or oxygen, Ra and Rb are each independently hydrogen, $C_{1-5}$ alkyl, $C_{3-8}$ cycloalkyl, or Ra and Rb together with the atoms to which they are attached form a ring which is optionally substituted with 1-6 substituents. Reaction of the compound of formula V with a methylene equivalent such as, but not limited to, dichloromethane, in the presence of a suitable base such as metal $C_{1-5}$ dialkylamides or metal $C_{1-5}$ dialkyl bases, in a suitable solvent, in the presence of an oxidizing agent such as, but not limited to, hydrogen peroxide, to provide a carboxaldehyde of formula VI. Reaction of the carboxaldehyde of formula VI with hydroxylamine, in a suitable solvent, provides an oxime of formula VII. Reaction of the oxime of formula VII with an acid such as hydrogen chloride followed by the reaction with reagents such as N-chlorosuccinimide and ammonium hydroxide, in a suitable solvent, provides a carboxamidine of formula I.

Synthetic Example
Overall Scheme
Process I
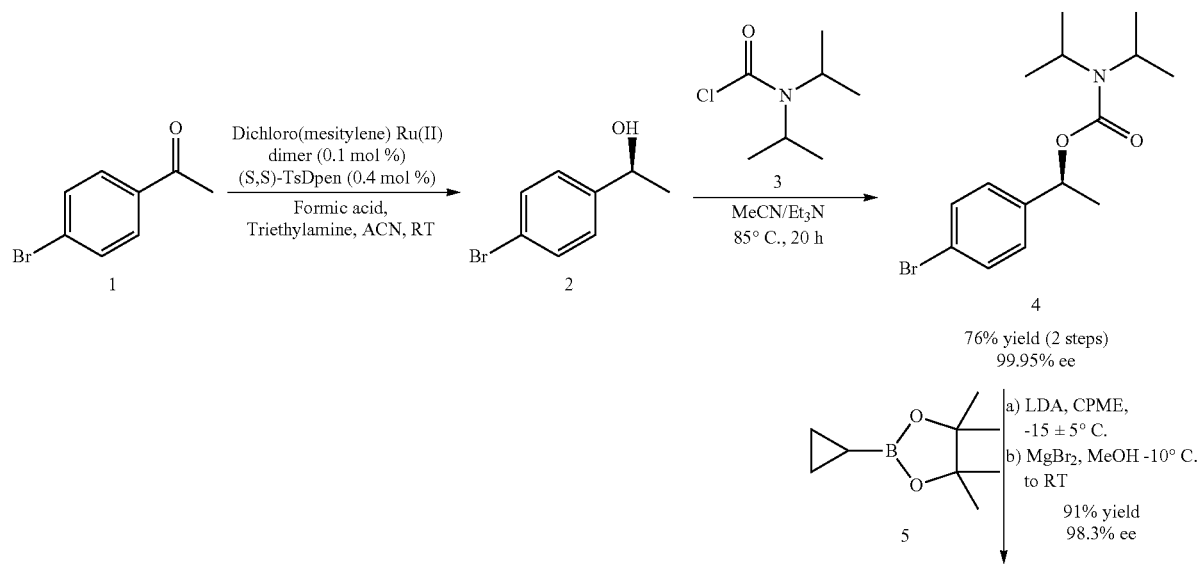
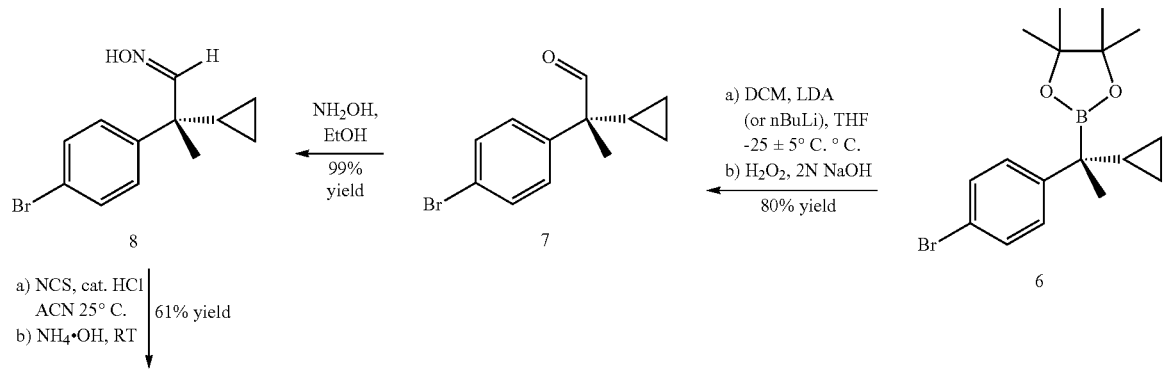
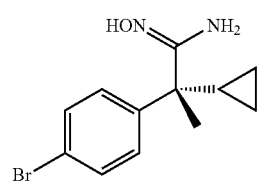

Overall Scheme
Process II
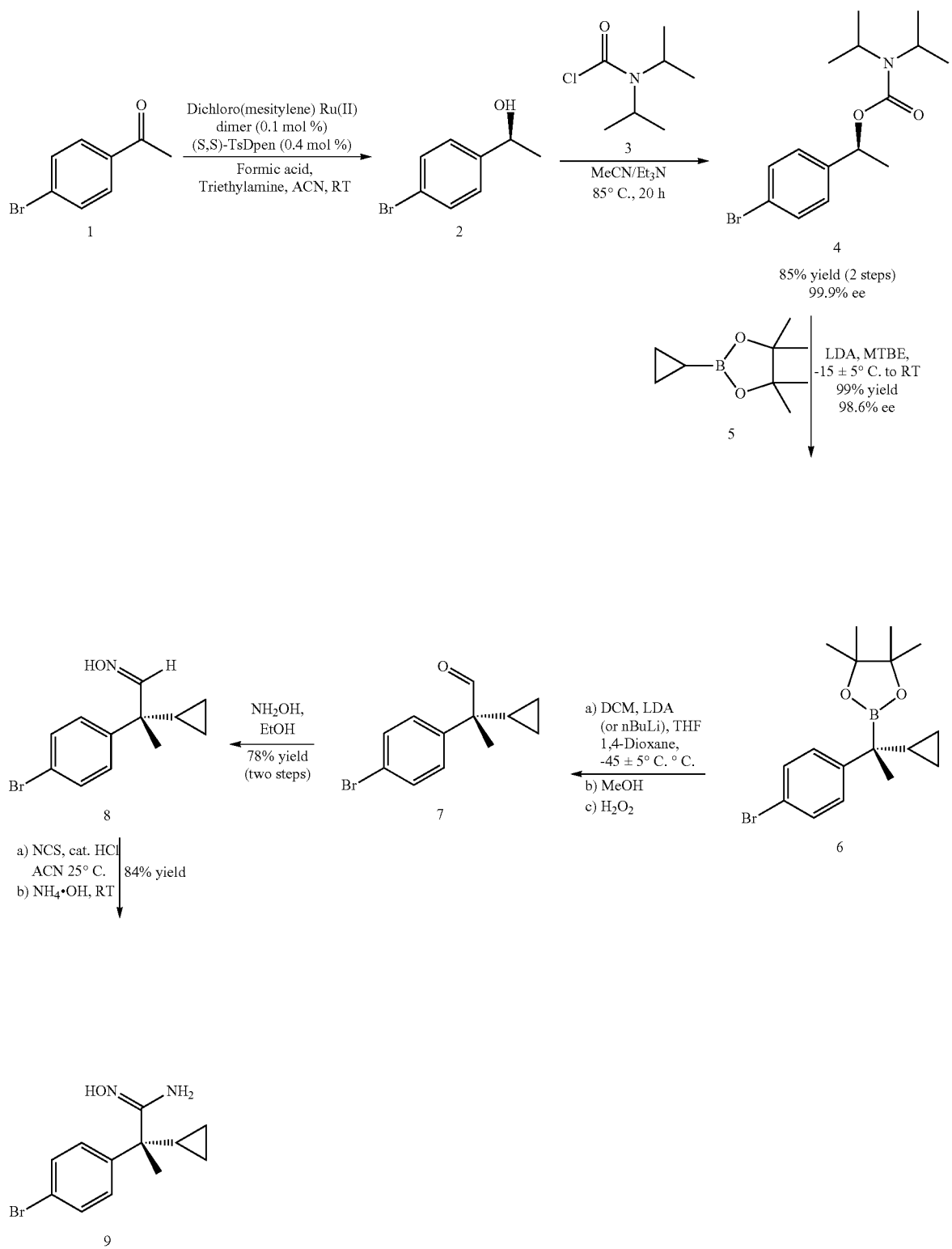

Process I

Experimentals

Preparation of (S)-1-(4-bromophenyl)ethyl diisopropylcarbamate (4)

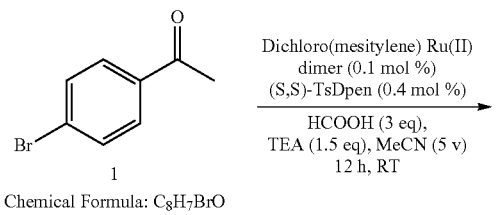

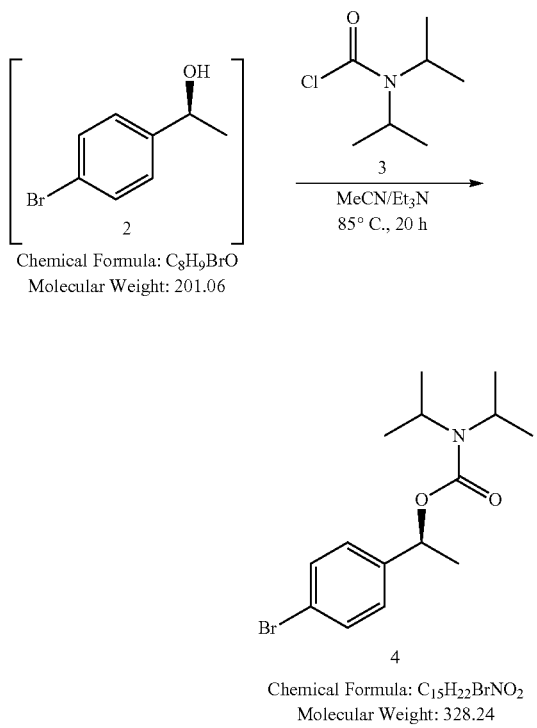

Preparation of (S)-1-(4-bromophenyl)ethanol (2)

To a clean and dry reactor (5 L, reactor 1) under an inert atmosphere (nitrogen) is charged acetonitrile (4.42 Kg). The resulting solution is degassed with nitrogen for 15 min. To the 5 L reactor (reactor 1) is charged dichloro(mesitylene)Ru(II) dimer (13.37 g, 0.023 mol, 0.001 equiv) and (S,S)-TsDpen ((1S,2S)-(+)-N-p-Tosyl-1,2-diphenylethylenediamine, 32.84 g, 0.090 mol, 0.004 equiv). Reactor 1 is degassed with nitrogen for 15 min and then degassed acetonitrile (2.65 Kg) followed by triethylamine (0.65 Kg, 6.42 mol, 0.28 equiv) is charged to the reactor. The resulting solution is agitated at an internal temperature of 22±5° C. until a clear red solution is obtained (~15 min). To a separate clean and dry 50 L reactor (reactor 2) with an attached gas dispersion tube under an inert atmosphere is charged 4'-bromoacetophenone (4.50 Kg, 22.6 mol, 1.00 equiv) and the reactor is purged with nitrogen 3-times. Acetonitrile (13.26 Kg) is charged to the reactor (reactor 2). The batch is agitated at an internal temperature of 22±5° C. The batch temperature of reactor 2 is adjusted to an internal temperature of 0±3° C. and during this cooling period triethylamine (3.0 kg, 29.6 mol, 1.31 equiv) is charged to the batch. To reactor 2 is charged formic acid (3.22 Kg, 68.6 mol, 3.00 equiv) subsurface at a rate to maintain the internal temperature at NMT 15° C. The batch is then purged with nitrogen for 15 min. Through a clean and dry transfer line the solution from reactor 1 (5 L) is transferred to the 50 L reactor (reactor 2) at an internal temperature of ~15° C. Reactor 1 (5 L) is washed with acetonitrile (1.76 Kg) and this solution is transferred via the transfer line into reactor 2 (50 L). The batch temperature (reactor 2) is adjusted to an internal temperature of 20±5° C. The batch is agitated with nitrogen purging through the dispersion tube at an internal temperature of 20±5° C. for 12-15 h or until HPLC analysis shows the conversion (220 nm) is >98.5 A % (this experiment: 18 h, 99.53 A % conversion and 96.0% ee). The batch temperature (reactor 2) is adjusted to an internal temperature of 55±5° C. and acetonitrile is removed by vacuum distillation (internal temperature during the distillation, ~45° C.) to remove 21.2 L of acetonitrile, which the batch volume is adjusted to ~7.8 L (1.7 vols). To the batch is charged ethyl acetate (6.08 Kg) and the distillation is continued until the batch volume is adjusted to ~9.0 L (2 vols). To the batch is charged ethyl acetate (28.4 Kg) and water (9.0 Kg). The batch is agitated at an internal temperature of 20±5° C. for 5 min and then the layers allowed to separate. The aqueous layer is cut (mass of aqueous layer: 10.86 Kg). To the batch is charged a 5 wt % aqueous solution of sodium bicarbonate (9.45 Kg, made by dissolving 0.45 Kg of sodium bicarbonate in 9.0 Kg of water). The batch is agitated at an internal temperature of 20±5° C. for 5 min and then the layers are allowed to separate. The aqueous layer is cut (mass of aqueous layer: 9.40 Kg). The batch temperature is adjusted to an internal temperature of 55° C. and ethyl acetate is removed by vacuum distillation (internal temperature of 45° C. during the distillation) to adjust the batch volume to ~6.75 L (1.5 vols, removed 20.2 L solvent). To the batch is charged acetonitrile (12.38 Kg) and the distillation is continued to adjust the batch volume to 11.3 L (2.5 vols). A sample is removed and HPLC A % purity, KF (criteria NMT 2000 ppm), and ee are determined). For this batch: 99.53 A % purity (220 nm), KF=217 ppm water, and Chiral HPLC: 96.0% ee for (S)-1-(4-bromophenyl)ethanol (2). The batch is used as is for the next step.

Preparation of (S)-1-(4-bromophenyl)ethyl diisopropylcarbamate (4)

To a clean and dry reactor (reactor 1) under an inert atmosphere (nitrogen) is charged N,N-diisopropylcarbamoyl chloride (3, 4.48 Kg, 27.4 mol, 1.22 equiv) and acetonitrile (10.6 Kg). To a separate reactor (reactor 2) is charged (S)-1-(4-bromophenyl)ethanol (2) (4.50 Kg in ~9.0 L of acetonitrile). The N,N-diisopropylcarbamoyl chloride acetonitrile solution from reactor 1 is charged into reactor 2 at an internal temperature of 20±5° C. Reactor 1 is rinsed with acetonitrile (3.5 Kg) and this solution is charged into reactor 2. To the batch (reactor 2) is charged triethylamine (3.40 Kg, 33.6 mol, 1.50 equiv) at an internal temperature of 20±5° C. The batch temperature is adjusted to an internal temperature of 80±5° C. (reflux of the acetonitrile solution) and the batch is agitated at this temperature for 15 h or until HPLC analysis indicates >98.5 A % conversion (220 nm, for this batch: 18 h, 98.9 A % conversion). Vacuum is applied and the batch is distilled (internal temperature ~50° C.) to adjust the batch volume to ~11 L (2.4 vols). To the batch is charged ethyl acetate (16.2 Kg) and the batch is distilled (internal temperature ~50° C.) to adjust the batch volume to ~11 L (2.4 vols). The batch temperature is adjusted to an internal temperature of 20±5° C. and ethyl acetate (24.4 Kg) is charged to the batch at an internal temperature of 20±5° C. To the batch is charged water (10 Kg) and the batch is agitated for 5 min. The layers are allowed to separate and the aqueous layer is cut (mass of aqueous cut: 14.3 Kg). To the batch is charged water (10 Kg) and the batch is agitated for 5 min. The layers are allowed to separate and the aqueous layer is cut (mass of aqueous cut: 12.6 Kg). The batch is then filtered through a Charcoal filter (Cuno Lot: 904236 with a celite plug). The reactor and then the charcoal filter are washed with ethyl acetate (2.0 Kg). This solution is transferred back to the reactor where the batch temperature is adjusted to an internal temperature of 55±5° C. The batch volume is adjusted via vacuum distillation to 9 L (2 vols). To the batch is charged methanol (14.2 Kg) and the batch volume is adjusted to ~9 L (2 vols) via vacuum distillation. A sample of the batch is removed and assayed (GC) for ethyl acetate (Target: NMT 0.5 wt % ethyl acetate). If the target wt % of ethyl acetate is not met, the methanol distillation is repeated. To the batch is charged methanol (9.6 Kg) and the batch temperature is adjusted to −3 to 0° C. To a separate vessel (reactor 3) is prepared a 2:1 by volume mixture of methanol and water (28.8 L methanol (22.8 Kg) and 14.4 Kg of water). The mixture is agitated to obtain a homogeneous solution. To the main batch (reactor 2) is charged a slurry of (S)-1-(4-bromophenyl)ethyl diisopropylcarbamate (4) in a 1:1 by volume mixture of methanol and water (0.050 Kg (S)-1-(4-bromophenyl)ethyl diisopropylcarbamate (4) seed crystals in 500 mL of methanol/water 1:1 mixture (prepared by the mixing of 250 mL of water and 250 mL of methanol) at an internal temperature of −3 to 0° C. The batch is agitated at an internal temperature of −3 to 0° C. for 40 min to develop a seed bed. To the batch (reactor 2) is charged the 2:1 mixture of methanol:water prepared in reactor 3 over a 3 h period at an internal temperature of −3 to 0° C. The batch is agitated at an internal temperature of −3 to 0° C. for NLT 1 h. In a separate vessel is prepared a 3:2 by volume mixture of methanol and water by the mixing Methanol (3.2 Kg, 4.04 L) and water (2.7 Kg). The product is collected by filtration. The product is rinsed with the 3:2 mixture of methanol and water prepared previously. The solids are suction dried for 1-2 h. The filter cake is loaded onto trays and the resulting material is dried in a vacuum oven (Temperature of oven NMT 20° C., the mp of the solids is ~39° C.). The solids are dried until the water content is <0.5 wt %. The solids massed 5.80 Kg and proton NMR wt % (with dimethyl fumarate as an internal standard) assay indicates 96.7 wt % (S)-1-(4-bromophenyl)ethyl diisopropylcarbamate (4) (76% yield over two steps), Chiral HPLC: 99.95% ee, HPLC purity: >99 A %, and KF: 125 ppm water.

Preparation of (S)-2-(1-(4-bromophenyl)-1-cyclopropylethyl)-4,4,5,5-tetramethyl-1,3,2-dioxaborolane (6)

4

Chemical Formula: $C_{15}H_{22}BrNO_2$
Molecular Weight: 328.24

+

5

Chemical Formula: $C_9H_{17}BO_2$
Molecular Weight: 168.04

1) LDA, CPME, -15 ± 5° C.
2) 1M MgBr$_2$ in MeOH, -10° C. to RT

6

Chemical Formula: $C_{17}H_{24}BBrO_2$
Molecular Weight: 351.09

To a clean, dry and nitrogen purged reactor (vessel 1) is charged (S)-1-(4-bromophenyl)ethyl diisopropylcarbamate (4, 1.00 Kg, 3.04 mol, 1.00 equiv). The reactor is purged with nitrogen. To the reactor (vessel 1) is charged Cyclopentyl methyl ether (8.60 Kg). The agitation is started and the batch is agitated at an internal temperature of 20±5° C. A sample is removed from the batch and the KF is determined (target: KF NMT 250 ppm water, for this batch: 64.4 ppm water). To the batch is charged 2-cyclopropyl-4,4,5,5-tetramethyl-1,3,2-dioxaborolane (5, 0.639 Kg, 3.74 mol, 1.25 equiv) at an internal temperature of 20±5° C. In a separate reactor (vessel 2) a ~1 M solution of LDA is prepared by the addition of n-butyl lithium (1.40 L, 0.970 Kg, 3.50 mol, 1.15 equiv) to a cooled solution (internal temperature of 0±5° C.) of diisopropylamine (0.369 Kg, 3.65 mol, 1.20 equiv) in cyclopentyl methyl ether (1.40 L, 1.20 Kg) at a rate to maintain the internal temperature NMT 20° C. The solution is agitated for NLT 15 min. The batch temperature (vessel 1) is adjusted to an internal temperature of −15±5° C. To the batch (vessel 1) is charged the prepared LDA solution (vessel 2) at a rate to maintain the internal temperature at −15±5° C. The batch is then agitated at an internal temperature of −15±5° C. for NLT 15 min (NMT 1 h). To a separate vessel (vessel 3) is prepared a ~1 M solution of MgBr$_2$ in methanol by the addition of magnesium bromide (0.279 Kg, 1.52 mol, 0.50 equiv) to precooled (0° C.) methanol (1.50 L, 1.19 Kg) at a rate to maintain the internal temperature NMT 20° C. The resulting solution is agitated at an internal temperature of 20±5° C. for NLT 15 min. To the batch (vessel 1) is charged the 1 M magnesium bromide solution (vessel 3) at a rate to maintain the internal temperature at −15±5° C. The batch temperature is adjusted to an internal temperature of 10±5° C. and the batch is agitated at an internal temperature of 10±5° C. for NLT 60 min. To a separate reactor (vessel 4) is prepared a 5 wt % aqueous solution of citric acid by mixing citric acid (0.273 Kg) with water (5.23 Kg). The solution is mixed until a homogeneous solution is obtained (5 min). To the batch is charged the 5 wt % aqueous citric acid solution (vessel 4) at an internal temperature of 20±5° C. The batch is agitated at an internal temperature of 20±5° C. for 5 min. The layers are allowed to settle and the aqueous layer is cut (mass of aqueous cut: 7.59 Kg). To the batch is charged water (4.0 Kg) at an internal temperature of 20±5° C. The batch is agitated at an internal temperature of 20±5° C. for 20 min. The layers are allowed to settle and the aqueous layer is cut (mass of aqueous cut: 5.95 Kg). The batch volume is adjusted to ~2 L (~2 vols) via vacuum distillation (external temperature: NMT 65° C., mass of the distillate is 9.5 Kg). The batch is filtered through a celite plug. The reactor is washed with cyclopentyl methyl ether (1.7 Kg) and this solution is used to rinse the celite plug. The two solutions are combined. The mass of the combined solutions: 3.20 Kg (HPLC A % purity at 220 nm: 90 A %; KF: 2000 ppm water; Chiral HPLC: 98.3% ee; Proton NMR wt % assay with dimethyl fumarate as an internal standard: 29.9 wt % (S)-2-(1-(4-bromophenyl)-1-cyclopropylethyl)-4,4,5,5-tetramethyl-1,3,2-dioxaborolane (6), 0.955 Kg, 90.9% yield). The cyclopentyl methyl ether solution of 6 was used as is for the next step.

Preparation of (R)-2-(4-bromophenyl)-2-cyclopropylpropanal (7)

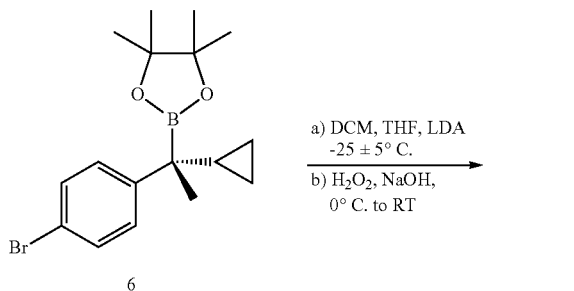

6
Chemical Formula: C$_{17}$H$_{24}$BBrO$_2$
Molecular Weight: 351.09 a) DCM, THF, LDA
−25 ± 5° C.
b) H$_2$O$_2$, NaOH,
0° C. to RT

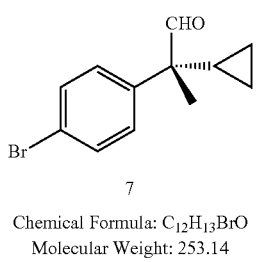

7
Chemical Formula: C$_{12}$H$_{13}$BrO
Molecular Weight: 253.14

To a clean and dry 2 L reactor (vessel 1) under an inert atmosphere (nitrogen) is charged the (S)-2-(1-(4-bromophenyl)-1-cyclopropylethyl)-4,4,5,5-tetramethyl-1,3,2-dioxaborolane solution (6, 200.0 g, 24.0 wt %, 136.7 mmol, 1.00 equiv). A sample is removed and the KF is determined (target KF<350 ppm water, if >350 ppm water proceed with an azeotropic cyclopentyl methyl ether distillation). The KF of this batch was determined to be 750 ppm water, and 200 mL of cyclopentyl methyl ether was charged to the batch. The batch was vacuum distilled (external temperature <60° C.) to reduce the batch volume to 200 mL. The KF of the batch after the azeotropic distillation is: 103 ppm water. To the batch is charged tetrahydrofuran (222 g) and then the batch temperature was adjusted to an internal temperature of −25±5° C. During the cooling of the batch dichloromethane (78.9 mL, 1230 mmol, 9.0 equiv) was charged. To a separate reactor (vessel 2) was prepared the LDA solution via the following procedure: To a clean and dry reactor (1 L) under an inert atmosphere was charged tetrahydrofuran (200 mL) and diisopropylamine (78.6 mL, 560.5 mmol, 4.10 equiv). The batch temperature was adjusted to −5° C. and to the agitated solution was charged 2.4 M solution of n-butyl lithium (227.8 mL, 546.9 mmol, 4.00 equiv) at a rate to maintain the internal temperature NMT 25° C. The resulting solution was stirred at an internal temperature of 20±5° C. for NLT 15 min. The LDA solution is cooled to an internal temperature of −25±5° C. To the main batch (vessel 1) is charged the precooled (an internal temperature of −25±5° C.) LDA solution (vessel 2) at a rate to maintain the batch temperature NMT −11° C. and with a 25 min addition time. The batch is aged at an internal temperature of −25±5° C. for 30 min (NLT 20 min). The batch temperature was adjusted to an internal temperature of 0±5° C. and the batch is aged at an internal temperature of 0±5° C. for 1 h. To a separate vessel (vessel 3) is prepared the sodium hydroxide/hydrogen peroxide solution as follows: charge sodium hydroxide (12.0 g, 300.7 mmol, 2.2 equiv) and water (150 g). The solution is mixed to obtain a homogeneous solution. To the homogeneous sodium hydroxide solution is charged hydrogen peroxide (30%, 17.1 g, 150.4, 1.1 equiv). The solution is agitated to form a clear homogeneous solution. To the main batch (vessel 1) is charged the sodium hydroxide/hydrogen peroxide solution (vessel 3) at a rate to maintain the internal temperature <25° C. Note; the exotherm from the hydrogen peroxide charged is delayed by ~1-2 mins, thus portion-wise charging is usually performed. The batch is agitated at an internal temperature of 20±5° C. for 30 min. The agitation is stopped and a sample is removed for HPLC analysis (target >95A % conversion from the rearrangement products to the aldehyde). If the oxidation is not complete, continue agitation for an additional 30 min and recheck HPLC A % conversion. To a separate vessel (vessel 4) is prepared a ~4 N HCl aqueous solution by mixing concentrated aqueous hydrogen chloride (177.4 g) with water (273 g) until the solution is homogeneous. To the batch is charged 250 g of the ~4 N aqueous HCl solution (vessel 4) at a rate to maintain the internal temperature <25° C. The batch is agitated at an internal temperature of 20±5° C. for 10 min. The agitation is stopped and the layers are allowed to settle (~30 min). The aqueous layer is cut (mass: 550 g). To the batch is charged 200 g of the ~4 N aqueous HCl solution (vessel 4) at a rate to maintain the internal temperature <25° C. The batch is agitated at an internal temperature of 20±5° C. for 10 min. The agitation is stopped and the layers are allowed to settle (~30 min). The aqueous layer is cut (mass: 297 g). To a separate vessel (vessel 5) is prepared a 5 wt % NaCl aqueous solution by dissolving sodium chloride (10.0 g) in water (190.0 g). To the batch is charged the 5 wt % sodium chloride solution (vessel 5). The batch is agitated at an internal temperature of 20±5° C. for 10 min. The agitation is stopped and the layers are allowed to settle (~30 min). The aqueous layer is cut (mass: 233 g). The batch volume is adjusted to ~100 mL via vacuum distillation (external temperature <50° C.). The batch is drained and filtered through a celite plug. The reactor is rinsed with reagent grade alcohol (~150 mL). This rinse is used to rinse the celite plug and combined with the main batch solution. The combined mass of the solution: 233 g. Proton NMR wt % assay with an internal standard (dimethyl fumarate) indicates 11.9 wt % of (R)-2-(4-bromophenyl)-2-cyclopropylpropanal (7, 27.7 g, 80% yield). This solution is used as is for the following step.

Preparation of (R)-2-(4-bromophenyl)-2-cyclopropylpropanal oxime (8)

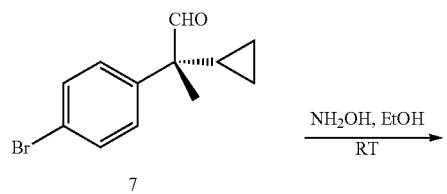

7
Chemical Formula: C₁₂H₁₃BrO
Molecular Weight: 253.14

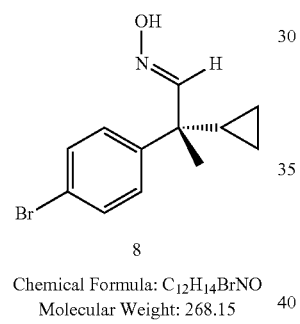

8
Chemical Formula: C₁₂H₁₄BrNO
Molecular Weight: 268.15

To a 500 mL reactor is charged the crude solution of (R)-2-(4-bromophenyl)-2-cyclopropylpropanal (7, 230 g, 11.9 wt %, 108.1 mmol, 1.00 equiv). The batch is reduced to 75 mL (3 vols) via vacuum distillation (external temperature NMT 55° C.). To the batch is charged ethanol (denatured, 78.9 g, 100 mL, 4 vols). The batch is reduced to 75 mL (3 vols) via vacuum distillation (external temperature NMT 55° C.). To the batch is charged ethanol (denatured, 39.5 g, 50 mL, 2 vols). The batch temperature is adjusted to an internal temperature of 10±5° C. To the batch is charged 50 wt % Hydroxylamine (10.7 g, 162.2 mmol, 1.50 equiv) at a rate to maintain the internal temperature of the batch <30° C. The batch is then agitated at an internal temperature of 20±5° C. for 2 h. An HPLC sample is removed to determine conversion (target >97 A % conversion 220 nm, for this batch: >99.5 A % conversion). To a separate vessel (vessel 2) is prepared the 5 wt % aqueous sodium chloride solution by dissolving sodium chloride (7.5 g) in water (142.5 g). To the batch is charged isopropyl acetate (157 g, 180 mL, 7 vols) and 5 wt % aqueous sodium chloride (75 g, ~3 vols, vessel 2). The batch is agitated for 20 min and then the layers are allowed to settle. The aqueous layer is cut. To the batch is charged 5 wt % aqueous sodium chloride (75 g, ~3 vols, vessel 2). The batch is agitated for 20 min and then the layers are allowed to settle. The aqueous layer is cut. The batch volume is adjusted to 2-3 vols (50-75 mL) via vacuum distillation (external temperature NMT 55° C.). To the batch is charged acetonitrile (39.3 g, 50 mL, ~2 vols). The batch volume is adjusted to 2 vols (50-75 mL) via vacuum distillation (external temperature NMT 55° C.). The batch was drained and the reactor rinsed with acetonitrile (3.9 g, 5 mL). The rinse is combined with the original batch and the resulting solution reduced to ~50 mL via vacuum distillation. The mass of the resulting solution: 44.4 g and the Proton NMR wt % assay (with dimethyl fumarate as an internal standard) is 65 wt % (28.9 g, 99.5% yield) of (R)-2-(4-bromophenyl)-2-cyclopropylpropanal oxime (8). The solution is used as is for the following step.

Preparation of (R)-2-(4-bromophenyl)-2-cyclopropyl-N'-hydroxypropanimidamide (9)

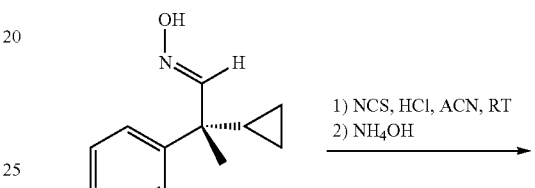

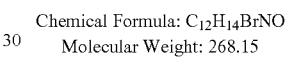

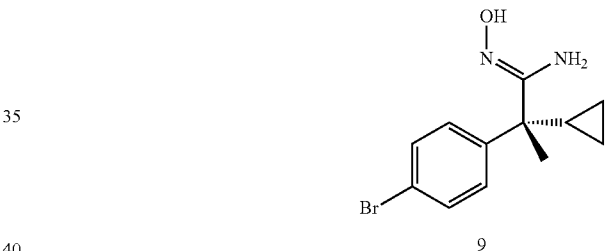

9
Chemical Formula: C₁₂H₁₅BrN₂O
Molecular Weight: 283.16

To clean and dry reactor (vessel 1) is charged (R)-2-(4-bromophenyl)-2-cyclopropylpropanal oxime (8, 10.0 g, 24 wt %, 24.2 mmol, 1.00 equiv). To the solution is charged acetonitrile (30 mL). The resulting solution is cooled to an internal temperature of 10±5° C. To the solution is charged 3M hydrogen chloride solution in cyclopentyl methyl ether (0.80 mL, 2.4 mmol, 0.1 equiv). To a separate vessel (Vessel 2) is charged N-chlorosuccinimide (5.12 g, 36.3 mmol, 1.55 equiv) and acetonitrile (25 mL). The solution is agitated to form a slurry. To the batch at an internal temperature of 10±5° C. is charged the N-chlorosuccinimide solution (vessel 2) as a slurry at a rate to maintain the internal temperature NMT 25° C. An HPLC sample is removed and the HPLC conversion to the chloro-oxime is determined (Target >95 A % conversion). To the batch was charge ammonium hydroxide (28.7%, 7.39 g, 60.6 mmol, 2.50 equiv) at an internal temperature of 5±5° C. Note a small exotherm is observed due to the neutralization of the HCl. To the batch is charged water (10.0 g, 1.5 vols). The batch is agitated at an internal temperature of 20±5° C. for 15 h, or until HPLC analysis shows >95 A % conversion. To the batch is charged concentrated hydrogen chloride (37%, 12.0 g, 10.0 mL) and then heptane (34.2 g, 50 mL) and methyl tert-butyl ether (37.0 g, 50 mL).

Agitation is initiated and to dissolve the remaining inorganic solids, water (25 g) is charged to the batch. The batch is agitated at an internal temperature of 20±5° C. for 10 min and the layers are allowed to settle. The bottom layer (ACN/water) is cut and the top (heptane/MTBE) layer is removed. The bottom ACN/water layer is charged back into the reactor. To the batch is charged isopropyl acetate (21.8 g, 25.0 mL) followed by 45 mL of ~4N aqueous sodium hydroxide (prepared by dissolving 7.2 g sodium hydroxide in 45 mL water). The batch is agitated at an internal temperature of 20±5° C. for 20 min. The layers are allowed to settle and the aqueous layer is cut. To the batch is charged water (40.0 g, 40.0 mL) and the batch is agitated at an internal temperature of 20±5° C. for 20 min. The layers are allowed to settle and the aqueous layer is cut. To the batch is charged isopropanol (55.0 g, 70.0 mL) and the batch volume is adjusted to 20 mL via vacuum distillation (external temperature NMT 60° C.). The batch temperature is adjusted to an internal temperature of 15±5° C. and then the batch is seeded with crystalline (R)-2-(4-bromophenyl)-2-cyclopropyl-N'-hydroxypropanimidamide (9, 50 mg) and the batch is agitated at an internal temperature of 15±5° C. for 30 min to form a seed bed. To the batch is charged heptane (100 mL, 68.4 g) over a 1 h period at an internal temperature of 15±5° C. The batch is agitated at an internal temperature of 15±5° C. for 60 min. The solids are collected by filtration and the filtrate is used to rinse the reactor. The solids are suction dried for 3 h and mass 4.2 g (HPLC A % purity 97.8 A %, 61% yield) of (R)-2-(4-bromophenyl)-2-cyclopropyl-N'-hydroxypropanimidamide (9).

Process II

Experimentals

Preparation of (S)-1-(4-bromophenyl)ethyl diisopropylcarbamate (4)

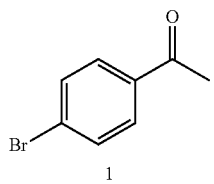

Dichloro(mesitylene) Ru(II) dimer (0.1 mol %)
(S,S)-TsDpen (0.4 mol %)
────────────────────→
HCOOH (3 eq),
TEA (1.6 eq), MeCN (5 v)
12 h, RT 1
Chemical Formula: $C_8H_7BrO$
Molecular Weight: 199.04

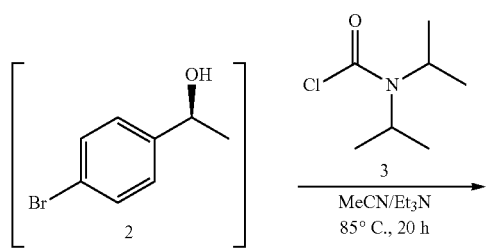

3
────────→
MeCN/Et$_3$N
85° C., 20 h

2
Chemical Formula: $C_8H_9BrO$
Molecular Weight: 201.06

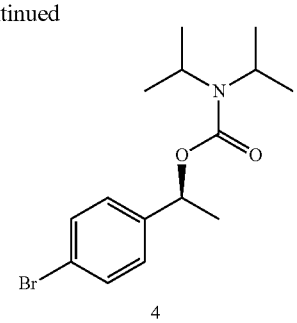

4
Chemical Formula: $C_{15}H_{22}BrNO_2$
Molecular Weight: 328.24

Preparation of (S)-1-(4-bromophenyl)ethanol (2)

To a clean and dry reactor (5 L, reactor 1) under an inert atmosphere (nitrogen) is charged acetonitrile (4.65 kg). The resulting solution is degassed with nitrogen for 15 min. To the 5 L reactor (reactor 2) is charged dichloro(mesitylene)Ru(II) dimer (24.0 g, 0.04 mol, 0.001 equiv) and (S,S)-TsDpen ((1S,2S)-(+)-N-p-Tosyl-1,2-diphenylethylenediamine, 58.0 g, 0.16 mol, 0.004 equiv). To the reactor 2 is charged degassed acetonitrile (4.10 kg) from reactor 1 followed by triethylamine (1.16 kg, 11.43 mol, 0.3 equiv). The resulting solution is agitated at an internal temperature of 22±5° C. for NLT 30 min. To a separate clean and dry 50 L reactor (reactor 3) with attached gas dispersion tube under an inert atmosphere is charged 4'-bromoacetophenone (7.88 kg, 39.42 mol, 1.00 equiv) and the reactor is purged with nitrogen 3-times. Acetonitrile (23.23 kg) is charged to the reactor (reactor 3). The batch is agitated at an internal temperature of 22±5° C. The batch temperature of reactor 3 is adjusted to an internal temperature of 0±3° C. and during this cooling period triethylamine (5.25 kg, 51.63 mol, 1.31 equiv) is charged to the batch. To reactor 3 is charged formic acid (5.67 kg, 118.25 mol, 3.00 equiv) subsurface at a rate to maintain the internal temperature at NMT 15° C. The batch is then purged with nitrogen for 15 min. Through a clean and dry transfer line the solution from reactor 2 (5 L) is transferred to the 50 L reactor (reactor 2) at an internal temperature of ~15° C. Reactor 2 (5 L) is washed with acetonitrile (0.55 kg) and this solution is transferred via the transfer line into reactor 3 (50 L). The batch temperature (reactor 3) is adjusted to an internal temperature of 20±5° C. The batch is agitated with nitrogen purging through the dispersion tube at an internal temperature of 20±5° C. for 12-15 h or until HPLC analysis shows the conversion (220 nm) is >98.5 A % (this experiment: 15 h, 99.53 A % conversion and 96.0% ee). The batch temperature (reactor 3) is adjusted to an internal temperature of 55±5° C. and acetonitrile is removed by vacuum distillation (internal temperature during the distillation, ~45° C.), to adjust the batch volume to ~12.6 L (1.6 vols). To the batch is charged ethyl acetate (14.22 kg) and the distillation is continued until the batch volume is adjusted to ~12.6 L (1.6 vols). To the batch is charged ethyl acetate (49.76 kg) and water (15.76 kg). The batch is agitated at an internal temperature of 20±5° C. for 5 min and then the layers are allowed to separate. The aqueous layer is cut (mass of aqueous layer: 17.04 kg). To the batch is charged a 5 wt % aqueous solution of sodium bicarbonate (15.55 kg, made by dissolving 0.811 kg of sodium bicarbonate in 14.97 kg of water). The batch is agitated at an internal temperature of 20±5° C. for 5 min and then the layers are allowed to separate. The aqueous layer is cut (mass of aqueous layer: 16.60 kg). The batch temperature is adjusted to an internal temperature of 55° C. and ethyl acetate is removed by vacuum distillation (internal temperature of 45° C. during the distillation) to adjust the batch volume to ~11.82 L (1.5 vols). To the batch is charged acetonitrile (22.92 kg) and the distillation is continued to adjust the batch volume to 15.76 L (2.0 vols). A sample is removed and HPLC A % purity, KF (criteria NMT 2000 ppm), and ee are determined). For this batch: 99.89 A % purity (220 nm), KF=217 ppm water, and Chiral HPLC: 96.0% ee for (S)-1-(4-bromophenyl)ethanol (2). The batch is used as is for the next step.

Preparation of (S)-1-(4-bromophenyl)ethyl diisopropylcarbamate (4)

To a clean and dry reactor (reactor 1) under an inert atmosphere (nitrogen) is charged N,N-diisopropylcarbamoyl chloride (3, 7.62 kg, 45.62 mol, 1.20 equiv) and acetonitrile (17.37 kg). To a separate reactor (reactor 2) is charged (S)-1-(4-bromophenyl)ethanol (2) (7.64 kg in ~12.92 L of acetonitrile). The N,N-diisopropylcarbamoyl chloride acetonitrile solution from reactor 1 is charged into reactor 2 at an internal temperature of 20±5° C. Reactor 1 is rinsed with acetonitrile (1.62 kg) and this solution is charged into reactor 2. To the batch (reactor 2) is charged triethylamine (5.80 kg, 57.03 mol, 1.50 equiv) at an internal temperature of 20±5° C. The batch temperature is adjusted to an internal temperature of 82±1° C. (reflux of the acetonitrile solution) and the batch is agitated at this temperature for 15 h or until HPLC analysis indicates >98.5 A % conversion (220 nm, for this batch: 18 h, 99.8 A % conversion). Vacuum is applied and the batch is distilled (internal temperature ~50° C.) to adjust the batch volume to ~15.28 L (2.0 vols). To the batch is charged ethyl acetate (35.16 kg) and the batch is distilled (internal temperature ~50° C.) to adjust the batch volume to ~19.86 L (2.6 vols). To the batch is charged ethyl acetate (41.37 kg) and then adjusted the batch temperature to 35±5° C. To the batch is charged water (16.82 kg) and the batch is agitated for 10 min. The layers are allowed to separate for NLT 30 min and the aqueous layer is cut (mass of aqueous cut: 21.60 kg). To the batch is charged water (16.82 kg) and the batch is agitated for 5 min. The layers are allowed to separate and the aqueous layer is cut (mass of aqueous cut: 17.32 kg). The batch is then filtered through a Charcoal filter (Cuno 55 carbon Lot: 904236 with a celite plug). The reactor and then the charcoal filter are washed with ethyl acetate (3.60 kg). This solution is transferred back to the reactor where the batch temperature is adjusted to an internal temperature of 55±5° C. The batch volume is adjusted via vacuum distillation to 15.28 L (2 vols). To the batch is charged methanol (24.19 kg) and the batch volume is adjusted to ~15.28 L (2 vols) via vacuum distillation. To the batch is charged methanol (16.33 kg) and a sample of the batch is removed and assayed (GC) for ethyl acetate (Target: NMT 0.5 wt % ethyl acetate). If the target wt % of ethyl acetate is not met, the methanol distillation is repeated. The batch temperature is adjusted to -3 to 0° C. To a separate vessel (reactor 3) is prepared a 2:1 by volume mixture of methanol and water (methanol (37.19 kg) and water (23.70 L). The mixture is agitated to obtain a homogeneous solution. To the main batch (reactor 2) is charged a slurry of (S)-1-(4-bromophenyl)ethyl diisopropylcarbamate (4) in a 1:1 by volume mixture of methanol and water (83 g seed crystals of (S)-1-(4-bromophenyl)ethyl diisopropylcarbamate (4) in 160 mL of methanol/water 1:1 mixture (prepared by the mixing of 80 mL of water and 80 mL of methanol) at an internal temperature of -3 to 0° C. The batch is agitated at an internal temperature of -3 to 0° C. for 40 min to develop a seed bed. To the batch (reactor 2) is charged the 2:1 mixture of methanol:water prepared in reactor 3 over a 3 h period at an internal temperature of -3 to 0° C. The batch is agitated at an internal temperature of -3 to 0° C. for NLT 1 h. In a separate vessel is prepared a 3:2 by volume mixture of methanol and water by the mixing Methanol (5.44 Kg, 6.88 L) and water (4.59 kg). The product is collected by filtration. The product is rinsed with the 3:2 mixture of methanol and water prepared previously. The solids are suction dried for 1-2 h. The filter cake is loaded onto trays and the resulting material is dried in a vacuum oven (Temperature of oven NMT 20° C., the mp of the solids is ~39° C.). The solids are dried until the water content is <0.5 wt %. The solids massed 11.26 kg and proton NMR wt % (with dimethyl fumarate as an internal standard) assay indicates 97.6 wt % (S)-1-(4-bromophenyl) ethyl diisopropylcarbamate (4) (85% yield over two steps), Chiral HPLC: 99.87% ee, HPLC purity: >99 A %, and KF: <100 ppm water.

Preparation of (S)-2-(1-(4-bromophenyl)-1-cyclopropylethyl)-4,4,5,5-tetramethyl-1,3,2-dioxaborolane (6)

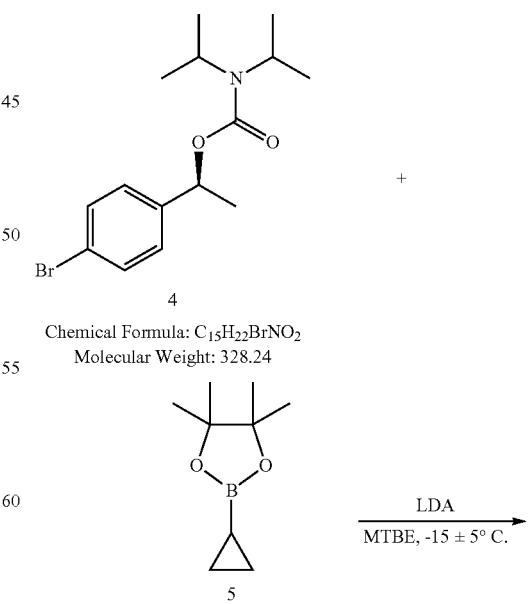

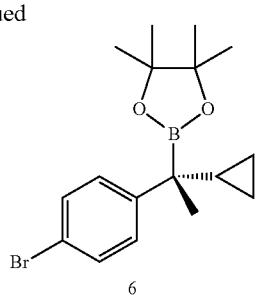

6

Chemical Formula: $C_{17}H_{24}BBrO_2$
Molecular Weight: 351.09

To a clean, dry and nitrogen purged reactor (vessel 1) is charged (S)-1-(4-bromophenyl)ethyl diisopropylcarbamate (4, 4.50 kg, 13.7 mol, 1.00 equiv). The reactor is purged with nitrogen. To the reactor (vessel 1) is charged tert-Butyl methyl ether (20.0 kg). The agitation is started and the batch is agitated at an internal temperature of 20±5° C. A sample is removed from the batch and the KF is determined (target: KF NMT 250 ppm water, for this batch: 217 ppm water). To the batch is charged 2-cyclopropyl-4,4,5,5-tetramethyl-1,3,2-dioxaborolane (5, 3.0 kg, 17.9 mol, 1.3 equiv) at an internal temperature of 20±5° C. In a separate reactor (vessel 2) a ~1 M solution of LDA is prepared by the addition of n-butyl lithium (6.87 L, 4.76 Kg, 17.2 mol, 1.25 equiv) to a cooled solution (internal temperature of 0±5° C.) of diisopropylamine (1.81 Kg, 17.9 mol, 1.30 equiv) in tert-Butyl methyl ether (6.87 L) at a rate to maintain the internal temperature NMT 20° C. The solution is agitated for NLT 15 min. The batch temperature (vessel 1) is adjusted to an internal temperature of −15±5° C. To the batch (vessel 1) is charged the prepared LDA solution (vessel 2) at a rate to maintain the internal temperature at −15±5° C. The batch is then agitated at an internal temperature of −15±5° C. for NLT 15 min (NMT 1 h). The batch temperature is adjusted to an internal temperature of 10±5° C. and the batch is agitated at an internal temperature of 10±5° C. for NLT 60 min. A HPLC sample is removed and the A % conversion (220 nm) is determined (target NLT 95A % conversion) for this batch: HPLC 98.5A % conversion. To a separate reactor (vessel 3) is prepared a 5 wt % aqueous solution of citric acid by mixing citric acid (0.90 kg) with water (17.1 kg). The solution is mixed until a homogeneous solution is obtained (5 min). To the batch is charged the 5 wt % aqueous citric acid solution (vessel 3) at an internal temperature of 20±5° C. The batch is agitated at an internal temperature of 20±5° C. for 15 min. The layers are allowed to settle and the aqueous layer is cut. To the batch is charged water (18 kg) at an internal temperature of 20±5° C. The batch is agitated at an internal temperature of 20±5° C. for 20 min. The layers are allowed to settle and the aqueous layer is cut. The batch volume is adjusted to ~11 L (~2 vols) via vacuum distillation (external temperature: NMT 65° C.). The batch is then drained into an appropriate container. To the reactor is charged 4.5 L of tert-butyl methyl ether and the reactor is agitated to efficiently rinse the reactor. The rinse solution is combined with the concentrated batch: the mass of the combined solutions: 9.84 kg (HPLC A % purity at 220 nm: 97.8 A %; KF: 0.06% water; Chiral HPLC: 98.6% ee; Proton NMR wt % assay with dimethyl fumarate as an internal standard: 48.8 wt % (S)-2-(1-(4-bromophenyl)-1-cyclopropylethyl)-4,4,5,5-tetramethyl-1,3,2-dioxaborolane (6), 4.80 Kg, 99.8% yield). The tert-butyl methyl ether solution of 6 was used as is for the next step.

Preparation of (R)-2-(4-bromophenyl)-2-cyclopropylpropanal (7)

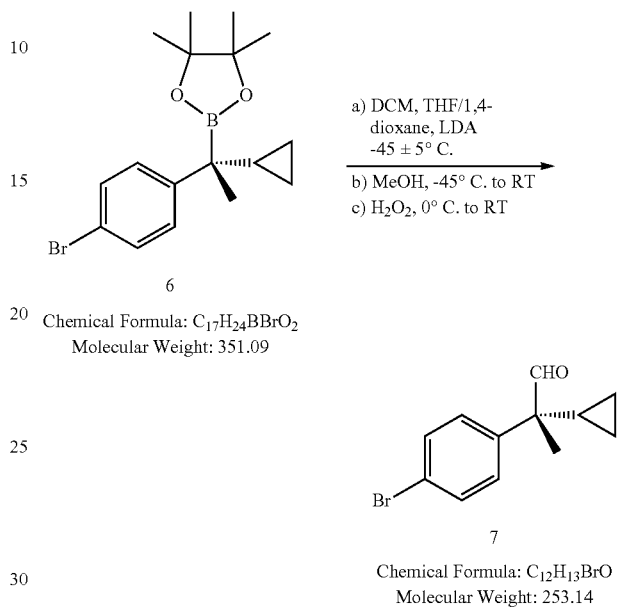

6

Chemical Formula: $C_{17}H_{24}BBrO_2$
Molecular Weight: 351.09 a) DCM, THF/1,4-dioxane, LDA
−45 ± 5° C.
b) MeOH, −45° C. to RT
c) $H_2O_2$, 0° C. to RT

7

Chemical Formula: $C_{12}H_{13}BrO$
Molecular Weight: 253.14

To a clean and dry 2 L reactor (vessel 1) under an inert atmosphere (nitrogen) is charged the (S)-2-(1-(4-bromophenyl)-1-cyclopropylethyl)-4,4,5,5-tetramethyl-1,3,2-dioxaborolane solution (6, 7.50 kg, 47 wt %, 10.0 mol, 1.00 equiv). The batch is concentrated via vacuum distillation ($T_{jacket}$ NMT 50° C.) to reduce the batch to ~7 L (~2 vols). To the batch is charged tetrahydrofuran (6 L) and agitation is initiated. The batch is concentrated via vacuum distillation ($T_{jacket}$ NMT 50° C.) to reduce the batch to ~5 L (~2 vols). To the batch is charged tetrahydrofuran (15 L) and then a sample is removed and the water content is determined: Target NMT 300 ppm: this batch 270 ppm. The batch volume at this point is ~21 L. To the batch is charged 1,4-dioxane 3.8 kg. The batch temperature was adjusted to −45±5° C. During the cooling of the batch dichloromethane (1.8 kg, 20 mol, 2.0 equiv) is charged. To the batch is charged a titrated 2 M solution of lithium diisopropylamine as a solution in THF, heptane and ethyl benzene (7.29 L, 5.75 kg, 15.4 mol, 1.5 equiv) at a rate to maintain the internal temperature NMT −40° C. (the addition required 1.5 h to complete). The batch is aged at −45±5° C. for NLT 20 min. To the batch is charged methanol (2.76 L, 2.18 kg) at a rate to maintain the internal temperature NMT −40° C. The batch temperature is adjusted to 20±5° C. and then the batch is aged at 20±5° C. for NLT 30 min. The batch is aged at an internal temperature of −25±5° C. for 30 min (NLT 20 min). The batch temperature was adjusted to an internal temperature of 0±5° C. To the main batch (vessel 1) is charged hydrogen peroxide solution (29-32 wt % aqueous: 1.22 kg, 10.76 mol, 1.05 equiv) at a rate to maintain the internal temperature <25° C. Note; the exotherm from the hydrogen peroxide charged is delayed by ~1-2 mins, thus portion-wise charging is usually performed. A sample is removed and the oxidation is monitored by HPLC analysis: Target NLT 95A %: this batch 96.5A %. To the batch is charged: 3.8 L of tert-butyl methyl ether and then 10 kg of a 4 N aqueous hydrogen chloride solution at a rate to maintain the internal temperature NMT 25° C. The resulting batch is agitated at 20±5° C. for 30 min (NMT 2 h). The agitation is stopped and the layers are allowed to settle (~30 min). The aqueous layer is cut (mass: 35.1 kg). To the batch is charged 4.6 kg of a 20 wt % solution of sodium sulfite (prepare by mixing 0.92 kg of sodium sulfite and 3.7 kg of water and mixing until homogeneous (20 nm)). The resulting batch is agitated at 20±5° C. for 30 min (NMT 2 h). The agitation is stopped and the layers are allowed to settle (~30 min). The aqueous layer is cut (mass: 5.28 kg). The batch is concentrated via vacuum distillation to ($T_{jacket}$ NMT 50° C.) to reduce the batch volume to ~5 L. The solution was retained in the reactor and used as is for the following step.

Preparation of (R)-2-(4-bromophenyl)-2-cyclopropylpropanal oxime (8)

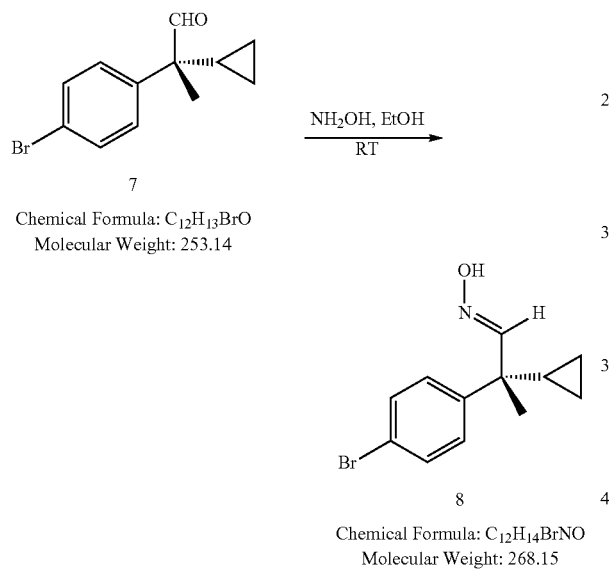

To the crude solution from the previous step (solution of (R)-2-(4-bromophenyl)-2-cyclopropylpropanal) retained in the reactor is charged 6.2 kg of 200 proof ethanol. The batch was then concentrated via vacuum distillation ($T_{jacket}$ NMT 50° C.) to ~7 L. To the batch was charged 6.2 kg of 200 proof ethanol. The batch temperature is then adjusted to 0±5° C. To the cooled batch is charged hydroxylamine (50 wt % aqueous solution, 1.0 kg, 15.4 mol, 1.5 equiv) at a rate to maintain the internal temperature of the batch <30° C. The batch is then agitated at an internal temperature of 20±5° C. for 2 h. An HPLC sample is removed to determine conversion (target >97 A % conversion 220 nm, for this batch: >99 A % conversion). To the batch is charged isopropyl acetate (19 kg) and 5 wt % aqueous sodium chloride (9.2 kg). The batch is agitated for 20 min and then the layers are allowed to settle. The aqueous layer is cut (mass aqueous cut 7.6 kg). To the batch is charged 5 wt % aqueous sodium chloride (9.2 kg). The batch is agitated for 20 min and then the layers are allowed to settle. The aqueous layer is cut (mass aqueous cut 14.5 kg). The batch volume is adjusted to 7 L via vacuum distillation (external temperature NMT 60° C.). To the batch is charged acetonitrile (10 L). The batch volume is adjusted to 7 L via vacuum distillation (external temperature NMT 60° C.). The batch was drained and the reactor rinsed with acetonitrile (2 L). The rinse was combined with the original batch and the resulting solution massed 7.75 kg (HPLC purity: 80.4 A % (220 nm), Karl Fisher 3.2% water and the Proton NMR wt % assay (with dimethyl fumarate as an internal standard) is 28.0 wt % (2.76 kg, 78.7% yield) of (R)-2-(4-bromophenyl)-2-cyclopropylpropanal oxime (8) for the two step process. The solution is used as is for the following step.

Preparation of (R)-2-(4-bromophenyl)-2-cyclopropyl-N'-hydroxypropanimidamide (9)

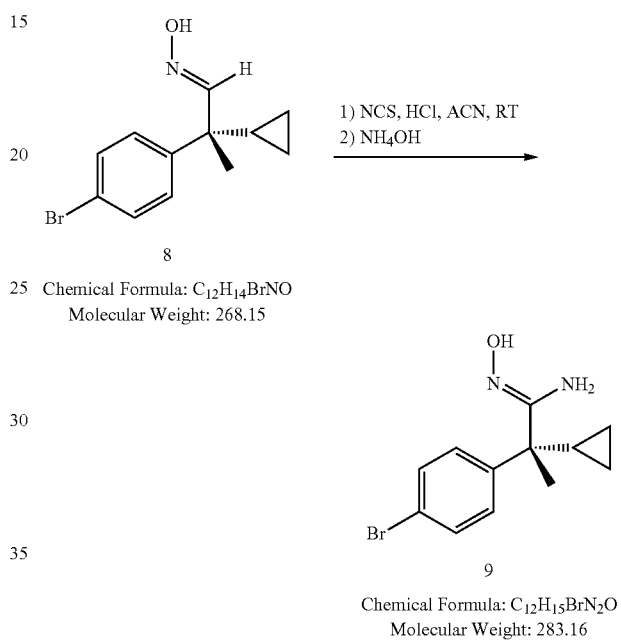

To clean and dry reactor (vessel 1) is charged (R)-2-(4-bromophenyl)-2-cyclopropylpropanal oxime (8, 21.5 kg, 21.46 wt %, 17.19 mol, 1.00 equiv, KF 3.0% water). To the solution is charged acetonitrile (21.5 L). The batch volume is adjusted to 2 vols (10 L) via vacuum distillation (external temperature NMT 55° C.) to afford final KF <0.1% water. The resulting solution is cooled to an internal temperature of 10±5° C. To the solution is charged concentrated HCl solution (0.278 kg, 3.44 mol, 0.2 equiv). To a separate vessel (vessel 2) is charged N-chlorosuccinimide (2.99 kg, 22.36 mol, 1.3 equiv) and acetonitrile (18.4 kg). The solution is agitated for NLT 30 min to form a clear solution. To the batch at an internal temperature of 10±5° C. is charged the N-chlorosuccinimide solution (vessel 2) at a rate to maintain the internal temperature NMT 25° C. An HPLC sample is removed and the HPLC conversion to the chloro-oxime is determined (Target >95 A % conversion). To the batch is charged aqueous ammonium hydroxide solution (28-30%, 4.18 kg, 35.78 mol, 2.08 equiv) at an internal temperature of 5±5° C. Note a small exotherm is observed due to the neutralization of the HCl. The batch is agitated at an internal temperature of 20±5° C. for 15 h, or until HPLC analysis shows >95 A % conversion. Cooled the batch to 10±5° C. and charged concentrated hydrogen chloride (~11.5M, 11.92 kg, 10.10 L) followed water (11.7 kg, 2.53 vols). To the batch is charged heptane (16 L) and methyl tert-butyl ether (7.8 L). The batch is agitated at an internal temperature of 20±5° C. for 10 min and the layers are allowed to settle. The bottom layer (ACN/water) is cut (mass of aqueous layer containing product: 63.42 kg) and the top (heptane/MTBE) layer is removed (mass of organic layer: 15.2 kg). The bottom ACN/water layer is charged back into the reactor. To the batch is charged isopropyl acetate (31 L) followed by 45 mL of aqueous sodium hydroxide (prepared by dissolving 10.18 kg sodium hydroxide in 26.4 L water) at an internal temperature of 20±5° C. The batch is agitated at an internal temperature of 20±5° C. for 20 min. The layers are allowed to settle and the aqueous layer is cut (mass of aqueous layer: 66.7). To the batch is charged water (11.8 kg) and the batch is agitated at an internal temperature of 20±5° C. for 10 min. The layers are allowed to settle and the aqueous layer is cut (mass of aqueous layer: 13.2 kg). To the batch is washed with water (2×30 kg) and the batch is agitated at an internal temperature of 20±5° C. for 10 min. The layers are allowed to settle and the aqueous layer is cut (mass of aqueous layers: 37.2 kg and 35.9 kg). The batch is heated (internal temperature 50±5° C.) and removed solvent via vacuum distillation to adjust the batch volume to 10 L. To the batch is charged isopropanol (20 L) and the batch volume is adjusted to 10 L via vacuum distillation (external temperature NMT 60° C.). To the batch is charged isopropanol (16 L) and the batch volume is adjusted to 10 L via vacuum distillation (external temperature NMT 60° C.). To the batch is charged Heptane (3.7 L) and adjusted the batch temperature to an internal temperature of 51±2° C. The batch is seeded with crystalline (R)-2-(4-bromophenyl)-2-cyclopropyl-N-hydroxypropan-imidamide (9, 50 g) (prepare slurry of 9 by mixing 50 g seeds to a pre-mixed solution of IPA (12.5 mL) and Heptane (12.5 mL)). Hold the batch at 48±2° C. for 15 min until the slurry is formed and then cooled the batch to 30±2° C. over 2 h. To the batch is charged heptane (12.06 kg) over 2 h period at an internal temperature of 30±5° C. Concentrated the batch via vacuum distillation (internal temperature NMT 35° C., external temperature NMT 43° C.) to adjust the batch vol. to ~14.5 L. The batch is cooled to an internal temperature of −5±2° C. over 2 h. The resulting slurry is stirred at internal temperature −5±2° C. for 1 h. The solids are collected at −5±2° C. by filtration and the filtrate is used to rinse the reactor. The solids are rinsed with cold pre-mixed 1:5 mixture of IPA and Heptane (prepare solution by mixing 0.6 kg IPA and 2.0 kg Heptane and store in a cold room for 2 h). The solids are suction dried for 3 h and then under vacuum with nitrogen stream at temperature 50±5° C. to afford mass 4.18 kg (For this batch, HPLC A % purity 99.05 A %, NMR wt %: 98.23%, Chiral HPLC: 99.05% ee, KF: 0.03% water and 84.5% yield) of (R)-2-(4-bromophenyl)-2-cyclopropyl-N'-hydroxypropa-nimidamide (9).

What is claimed is:

1. A process of making a compound of formula I:

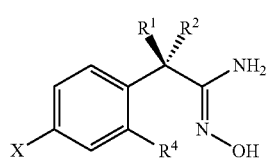

I the process comprising:
a) reducing a carbonyl compound of formula II under asymmetric reduction conditions selected from the group consisting of asymmetric hydrogenation and asymmetric transfer hydrogenation using, formic acid/triethylamine or potassium hydroxide/isopropyl alcohol, in the presence of a suitable catalyst, in a suitable solvent, to provide a compound of formula III:

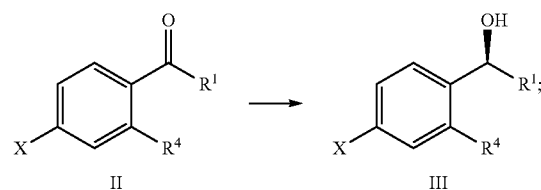

b) reacting the compound of formula III with a $C_{1-5}$ dialkylcarbamoyl chloride, in a suitable solvent, in the presence of a suitable base, to provide a carbamate of formula IV, wherein R is $C_{1-5}$ alkyl:

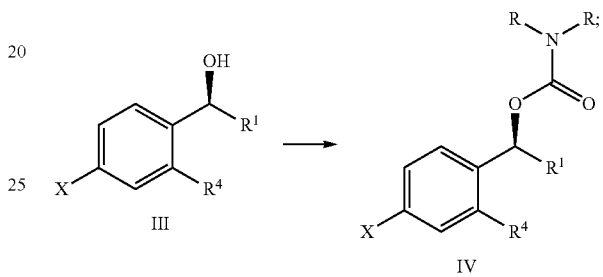

c) reacting the compound of formula IV with a suitable borane, boronic acid or boronic acid ester of the following formula $R^2$—$B(YRa)(YRb)$, in a suitable solvent, in the presence of a suitable metal-$C_{1-5}$dialkylamide or metal-disilyl$C_{1-5}$alkylamide base wherein the metal is lithium, sodium, potassium, calcium or magnesium, at a suitable temperature to provide an intermediate of formula V, wherein Y is a bond or oxygen, Ra and Rb are each independently hydrogen, $C_{1-5}$ alkyl, $C_{3-8}$ cycloalkyl, or Ra and Rb together with the atoms to which they are attached form a ring which is unsubstituted or substituted with 1-6 substituents selected from the group consisting of $C_{1-3}$ alkyl, $C_{3-6}$ cycloalkyl, and $C_{1-3}$ alkoxyl:

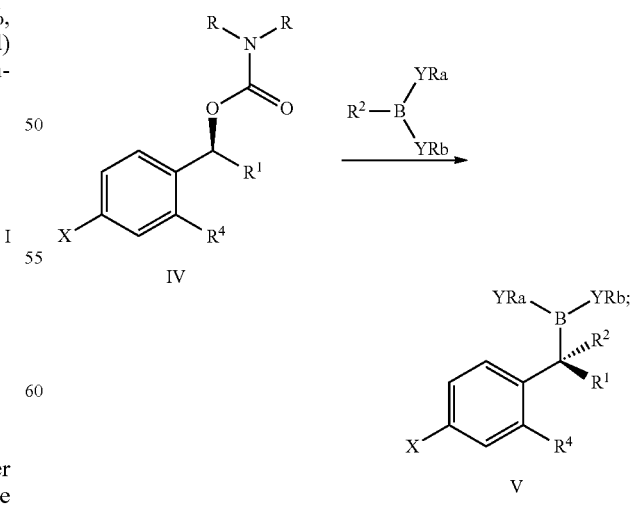

d) reacting the compound of formula V with a methylene equivalent in the presence of a suitable metal-$C_{1-5}$dialkylamide or metal-disilylC$_{1-5}$alkylamide base wherein the metal is lithium, sodium, potassium, calcium or magnesium, in a suitable solvent, in the presence of an oxidizing agent, to provide a carboxaldehyde of formula VI:

$$V \rightarrow VI$$

e) reacting the carboxaldehyde of formula VI with hydroxylamine, in a suitable solvent, to provide an oxime of formula VII:

$$VI \rightarrow VII$$

and f) reacting the oxime of formula VII with an acid, followed by the reaction with N-chlorosuccinimide and ammonium hydroxide, in a suitable solvent, to provide a carboxamidine of formula I:

$$VII \rightarrow I$$

wherein:

$R^1$ and $R^2$ are each independently hydrogen, C$_{1-7}$ alkyl or C$_{3-10}$ carbocycle, with the proviso that both $R^1$ and $R^2$ are not simultaneously hydrogen;

$R^4$ is hydrogen, C$_{1-3}$ alkyl, halogen or nitrile; and

X is bromo or iodo.

2. The process according to claim 1, wherein the asymmetric reduction condition in step (a) is asymmetric transfer hydrogenation using formic acid/base, wherein the base is selected from the group consisting of triethylamine and potassium hydroxide/isopropyl alcohol.

3. The process according to claim 1, wherein the suitable solvent in step (a) is acetonitrile, tetrahydrofuran, 1,4 dioxane or a mixture thereof.

4. The process according to claim 3, wherein the suitable solvent in step (a) is acetonitrile.

5. The process according to claim 1, wherein the suitable solvent in step (b) is acetonitrile, dichloromethane, tetrahydrofuran, dimethylformamide, N-methylpyrrolidinone, ethyl acetate, DMSO, 1,4 dioxane, isopropylacetate or a mixture thereof.

6. The process according to claim 5, wherein the suitable solvent in step (b) is dimethylformamide, N-methylpyrrolidinone, acetonitrile or a mixture thereof.

7. The process according to claim 1, wherein the suitable base in step (b) is 1,8-diazabicycloundec-7-ene (DBU), triethylamine, pyridine, 4-methylmorpholine, diisopropylethylamine or dimethylamine.

8. The process according to claim 7, wherein the suitable base in step (b) is triethylamine, 4-methylmorpholine, or diisopropylethylamine.

9. The process according to claim 1, wherein the suitable base in step (c) is lithiumdiisopropylamide (LDA), lithium hexamethyldisilazide (LiHMDS) or lithium tetramethylpiperidine (LiTMP).

10. The process according to claim 9, wherein the suitable base in step (c) is lithium diisopropylamide.

11. The process according to claim 1, wherein the suitable solvent in step (c) is diethyl ether, toluene, MTBE, cyclopentyl methyl ether, tetrahydrofuran, 1,4 dioxane, DME, diisopropyl ether, Me-THF or a mixture thereof.

12. The process according to claim 11, wherein the suitable solvent in step (c) is MTBE or cyclopentyl methyl ether.

13. The process according to claim 1, wherein the suitable base in step (d) is lithiumdiisopropylamide (LDA), lithium hexamethyldisilazide (LiHMDS) or lithium tetramethylpiperidine (LiTMP).

14. The process according to claim 13, wherein the suitable base in step (d) is lithium diisopropylamide.

15. The process according to claim 1, wherein the oxidizing agent used for step (d) is hydrogen peroxide, t-butyl-OOH or m-chloroperbenzoic acid.

16. The process according to claim 1, wherein the suitable solvent in step (d) is diethyl ether, toluene, MTBE, cyclopentyl methyl ether, tetrahydrofuran, 1,4 dioxane, toluene, heptane or a mixture thereof.

17. The process according to claim 1, wherein the suitable solvent in step (e) is methanol, ethanol, isopropyl alcohol, sec. butanol or a mixture thereof.

18. The process according to claim 1, wherein the suitable solvent in step (f) is acetonitrile, dichloromethane, tetrahydrofuran, 1,4 dioxane, diethyl ether or a mixture thereof.

19. The process according to claim 1, wherein in step (c), lithium diisopropylamide is added to a mixture of the boronic acid ester or boronic acid and the compound of formula IV, in a solvent selected from the group consisting of MTBE and cyclopentyl methyl ether, at a suitable temperature.

20. The process according to claim 19, wherein the suitable temperature is –20° C. to 20° C.

21. The process according to claim 1, wherein in step c), the stereochemistry is retained at or greater than 90% ee.

22. The process according to claim 1, wherein in step d), the stereochemistry is retained at or greater than 90% ee.

23. The process for making a compound of formula I, according to claim 1, wherein:

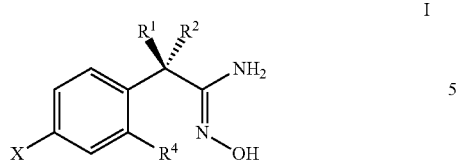
I
$R^1$ and $R^2$ are each independently methyl, ethyl, isopropyl, cyclopropyl, cyclobutyl or cyclopentyl;
$R^4$ is hydrogen, methyl or nitrile; and
X is bromo or iodo.
* * * * *